United States Patent
Warriner et al.

(10) Patent No.: US 11,027,931 B1
(45) Date of Patent: Jun. 8, 2021

(54) MARKER BAND LOCATOR SYSTEM

(71) Applicant: Blockwise Engineering LLC, Tempe, AZ (US)

(72) Inventors: Jeremiah J Warriner, Tempe, AZ (US); Ed Goff, Phoenix, AZ (US); Matthew Michael Bradley, Chandler, AZ (US)

(73) Assignee: Blockwise Engineering LLC, Tempe, AZ (US)

( * ) Notice: Subject to any disclaimer, the term of this patent is extended or adjusted under 35 U.S.C. 154(b) by 0 days.

(21) Appl. No.: 17/054,796

(22) PCT Filed: Feb. 1, 2020

(86) PCT No.: PCT/US2020/016300
§ 371 (c)(1),
(2) Date: Nov. 12, 2020

(51) Int. Cl.
*B65G 29/02* (2006.01)
*B65G 65/44* (2006.01)
*A61B 90/00* (2016.01)
*B65G 51/04* (2006.01)
*F15B 7/00* (2006.01)

(52) U.S. Cl.
CPC .............. *B65G 65/44* (2013.01); *A61B 90/39* (2016.02); *B65G 51/04* (2013.01); *F15B 7/00* (2013.01); *A61B 2090/3966* (2016.02)

(58) Field of Classification Search
CPC ........ B65G 65/44; B65G 15/02; B65G 29/02; B65G 47/525; B65D 83/0409; F15F 7/02
USPC ...... 198/438, 471.1, 482.1, 867.11; 221/188, 221/189, 211, 217; 414/415
See application file for complete search history.

(56) References Cited

U.S. PATENT DOCUMENTS

| | | | | |
|---|---|---|---|---|
| 3,387,746 A | * | 6/1968 | Whipple | A01C 7/044 221/211 |
| 3,757,995 A | | 9/1973 | Armstrong | |
| 4,069,930 A | | 1/1978 | Atwell | |
| 4,356,626 A | * | 11/1982 | Waghorn | B23P 19/001 29/747 |
| 4,744,455 A | | 5/1988 | Dragotta | |
| 5,097,940 A | * | 3/1992 | Manservigi | B65B 61/002 198/447 |
| 6,116,821 A | * | 9/2000 | Teoh | B23P 19/005 406/112 |
| 6,435,338 B1 | * | 8/2002 | Iwamoto | B65G 47/1485 198/396 |

(Continued)

*Primary Examiner* — Joseph A Dillon, Jr.
(74) *Attorney, Agent, or Firm* — Invention To Patent Services; Alex Hobson

(57) ABSTRACT

A marker band locator system locates a marker band, from a plurality of marker bands in a hopper, into a band receiver for further processing. A hopper is configured to loosely hold a plurality of marker bands and a band receiver, configured in an indexer, is configured under the hopper such that marker bands gravity feed down to the band receiver. A vacuum source produces a vacuum on the band receiver and if a marker band is properly located therein, the marker band forms a seal with the band receiver and the vacuum pressure exceeds a threshold vacuum pressure level. The indexer then actuates to a secondary position for further processing and removal of the marker band. If the vacuum pressure does not exceed the threshold, a burst of air jostles the marker bands in the hopper until a marker band is seated properly.

26 Claims, 10 Drawing Sheets

(56) References Cited

U.S. PATENT DOCUMENTS

| | | | | |
|---|---|---|---|---|
| 6,662,953 B1* | 12/2003 | Rouse | B65D 88/70 | 209/682 |
| 7,040,479 B2* | 5/2006 | Fochler | B65B 43/185 | 198/409 |
| 7,156,219 B2* | 1/2007 | Voigtmann | B29C 31/002 | 198/377.04 |
| 7,165,668 B2* | 1/2007 | Dombek | A24C 5/326 | 198/459.8 |
| 7,757,835 B2* | 7/2010 | Garthaffner | B65G 47/1428 | 198/392 |
| 7,886,566 B1 | 2/2011 | Knight et al. | | |
| 7,975,877 B2* | 7/2011 | Garthaffner | B65G 29/02 | 221/211 |
| 8,327,999 B2* | 12/2012 | Klaiber | B29C 49/4205 | 198/471.1 |
| 8,499,967 B2* | 8/2013 | Michelli | G07F 17/0092 | 221/278 |
| 8,651,320 B2* | 2/2014 | DuMond | G07F 17/0092 | 221/6 |
| 8,684,168 B2* | 4/2014 | Thiel | G01R 31/2893 | 198/471.1 |
| 8,752,261 B2 | 6/2014 | Van Sciver | | |
| 10,525,699 B2* | 1/2020 | Imai | B41J 3/4073 | |
| 2004/0020554 A1* | 2/2004 | Smith | B65B 1/366 | 141/67 |
| 2007/0068540 A1* | 3/2007 | Thomas | A24D 3/061 | 131/88 |
| 2013/0231586 A1* | 9/2013 | Tsonton | A61B 10/02 | 600/567 |
| 2013/0310845 A1* | 11/2013 | Thor | A61M 25/0122 | 606/127 |
| 2017/0197018 A1* | 7/2017 | Mukherjee | A61M 1/0031 | |
| 2018/0201447 A1* | 7/2018 | Viard | A61L 2/26 | |
| 2018/0360479 A1* | 12/2018 | Hofmann | A61M 25/0116 | |
| 2019/0233183 A1* | 8/2019 | Linton | B65D 77/20 | |

* cited by examiner

MARKER BAND LOCATOR SYSTEM

CROSS-REFERENCE TO RELATED APPLICATIONS

This application is a National Stage Entry of PCT application No. PCT/US2020/016300, filed on Feb. 1, 2020.

BACKGROUND OF THE INVENTION

Field of the Invention

The invention relates to a marker band locator system that locates a marker band from a plurality of marker bands in a hopper into a band receiver for further processing.

Background

Marker bands are located on medical devices to enable location of the medical device during surgery through fluoroscopy. These bands may be placed on either end of a medical device or catheter and during intravascular surgery, the leading and trailing ends of the device can be located in the body. The marker bands are very small and are typically sold in loose containers. Therefore, the marker bands have to be configured in a correct orientation before they can be place on a medical device. This process is often performed manually and is very tedious.

SUMMARY OF THE INVENTION

The invention is directed to a marker band locator system that locates a marker band from a plurality of marker bands in a hopper into a band receiver for further processing. The marker band locator system utilizes geometric positioning of a marker band into a shaped band receiver and gas pressure to determine if a marker band is seated properly in the band receiver. A hopper is configured to loosely hold a plurality of marker bands, and a band receiver, configured in an indexer, is configured under the hopper such that marker bands gravity feed down to the band receiver. A gas vacuum source produces a vacuum on the band receiver and if a marker band is properly located therein, the marker band forms an effective seal with the band receiver and the vacuum pressure exceeds a threshold vacuum pressure level. The indexer can then be actuated to a secondary position or location for further processing and removal of the marker band from the band receiver. The indexer can then be returned to the locating position under the hopper to receive another marker band. If the vacuum pressure does not rise above the threshold vacuum pressure level, then a marker band is not properly located in the band receiver and a burst of air from a gas pressure source moves an improperly positioned marker band out of the band receiver and jostles the marker bands in the hopper. When the marker bands settle back due to gravity, a marker band may properly seat in the band receiver. If not, as determined by the vacuum pressure check, another burst of gas again jostles the marker bands. This process is repeated until a marker band is properly located as determined by the vacuum pressure check.

An exemplary marker band is cylindrical in shape and has a conduit extending through the marker band. Marker bands may have an outer diameter of about 10 mm or less, 8 mm or less, about 5 mm or less, about 3 mm or less, about 2 mm or less, less than 1 mm, and any range between and including the outer diameter values provided.

The hopper may have a hopper funnel or tapering portion of the hopper that terminates at the outlet opening of the hopper. The band receiver inlet opening is configured under the outlet opening of the hopper when the indexer is in a locating position. The band receiver may be a recess in the indexer and may have curved surfaces for creating a seal with a properly positioned marker band therein.

A band receiver may have a curved seal surface along the bottom of the band receiver that has a radius of curvature effectively the same as the marker band outer diameter, to enable the vacuum source to produce vacuum pressure greater than the threshold vacuum pressure level when a marker band is properly positioned in the band receiver. When a marker band is properly positioned with a length axis aligned with the length axis of the curved seal surface, the outer diameter of the marker band may conform with the curved seal surface in the bottom of the band retainer, and when a vacuum is drawn on the bottom of the band retainer, such as through a port, the properly positioned marker band may be drawn down into contact with the curved seal surface, thereby producing a seal that results in a vacuum pressure above the threshold vacuum pressure level. When a marker band is not properly positioned and the length axis is not aligned with the length axis of the curved seal surface, or band receiving, vacuum is drawn on the bottom of the band retainer will not produce a vacuum that is above a threshold vacuum pressure level, as air will simply flow through the marker band conduit.

A band receiver may form a closed space when a marker band in properly positioned therein. The bottom of the band receiver may have the curved seal surface that forms a seal with the marker band and the front and back of the band receiver may have a cover to produce an effective seal with the first and second ends of the marker band. There may be small gaps that do not interfere with the vacuum source effectively producing a vacuum pressure that is above the threshold vacuum pressure level.

A band receiver may have a pressure port configured along a bottom portion of the band receiver for drawing vacuum for testing the position of a marker band. The pressure port may be configured in a pressure well, or recess extending from the band receiver. This recess may separate the pressure port from direct contact with marker band. A separate pressure port may be configured for producing a positive flow of gas into the band receiver to jostle the marker bands or a valve may be used to switch from vacuum to pressure.

In exemplary embodiment, a controller is coupled with the pressure gauge for checking the vacuum level, with the vacuum and pressure source and with the indexer actuator. The controller may automatically control the functions of the marker band locator system, wherein when the vacuum pressure is above a threshold vacuum pressure level, the controller initiates the indexer actuator to move the indexer, having a properly located marker band in the band receiver, to a secondary position. When the vacuum pressure is below the threshold vacuum pressure level, the controller may switch a valve to initiate a flow of gas into the band receiver to jostle the marker bands. This cycle of vacuum test and burst of air to jostle the marker bands may be very rapid, such as less than 1 second, or less than 0.5 seconds. The vacuum source and pressure source may be coupled with a pressure line that is fluidly coupled with the band receiver. A valve may be configured between the vacuum source, pressure source and the pressure line to control the flow of gas into and out of the band receiver. In an exemplary embodiment, a single pressure line extends to the pressure port. Again, the pressure port may be located along the bottom of the band receiver or in a pressure well that extends from the band receiver.

A properly located marker band may be moved to a secondary position of the indexer where it is removed from the band receiver or wherein the marker band is located on a medical device. A medical device may be inserted into the marker band and the marker band may be crimped down around the medical device. The medical device, and marker band coupled thereto, may then be removed thereby clearing the band receiver for receiving another marker band.

An indexer may be circular in shape and may have a plurality of band receivers configured around the circumference of the indexer for locating marker bands while previously located marker bands are subject to processing or removal from a secondary position. An indexer actuator may be a motor, such as a stepper motor that precisely moves the indexer from a locating position to a secondary position.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
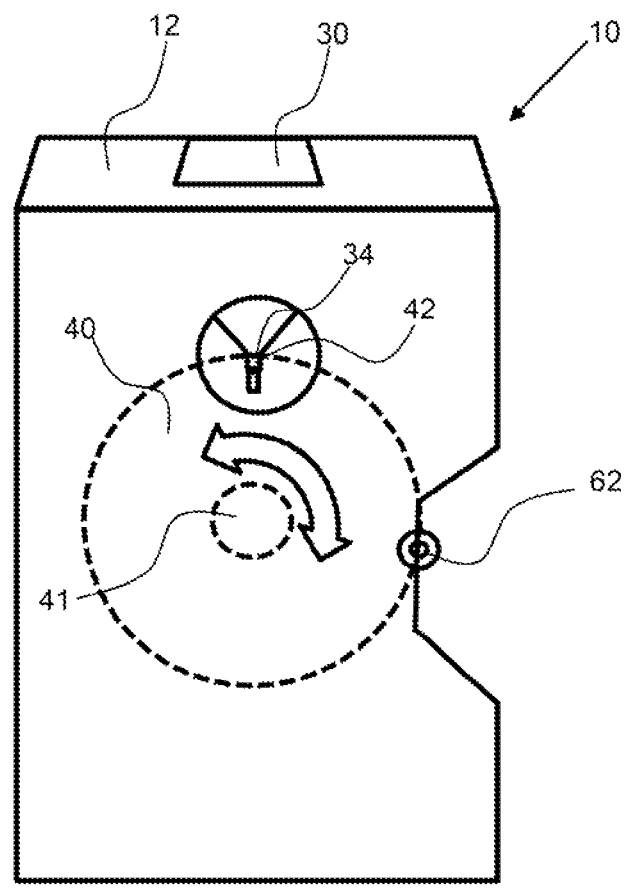
FIG. 1 shows a front view of an exemplary marker band locator system having a hopper and an indexer with a band receiver aligned with the outlet opening of the hopper to receive a marker band in the band receiver and configured to move a marker band in the band receiver to a secondary position.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

FIG. 1 shows a front view of an exemplary marker band locator system 10 having a hopper 30, configured in a housing 12, and an indexer 40 with a band receiver 42 aligned with the outlet opening 34 of the hopper to receive a marker band in the band receiver. An actuator 41, such as a stepper motor, may move the indexer from the band locator position, as shown, to a secondary position 62 for further processing, such as locating the band on a medical device and crimping the band thereon.

Figure 2:
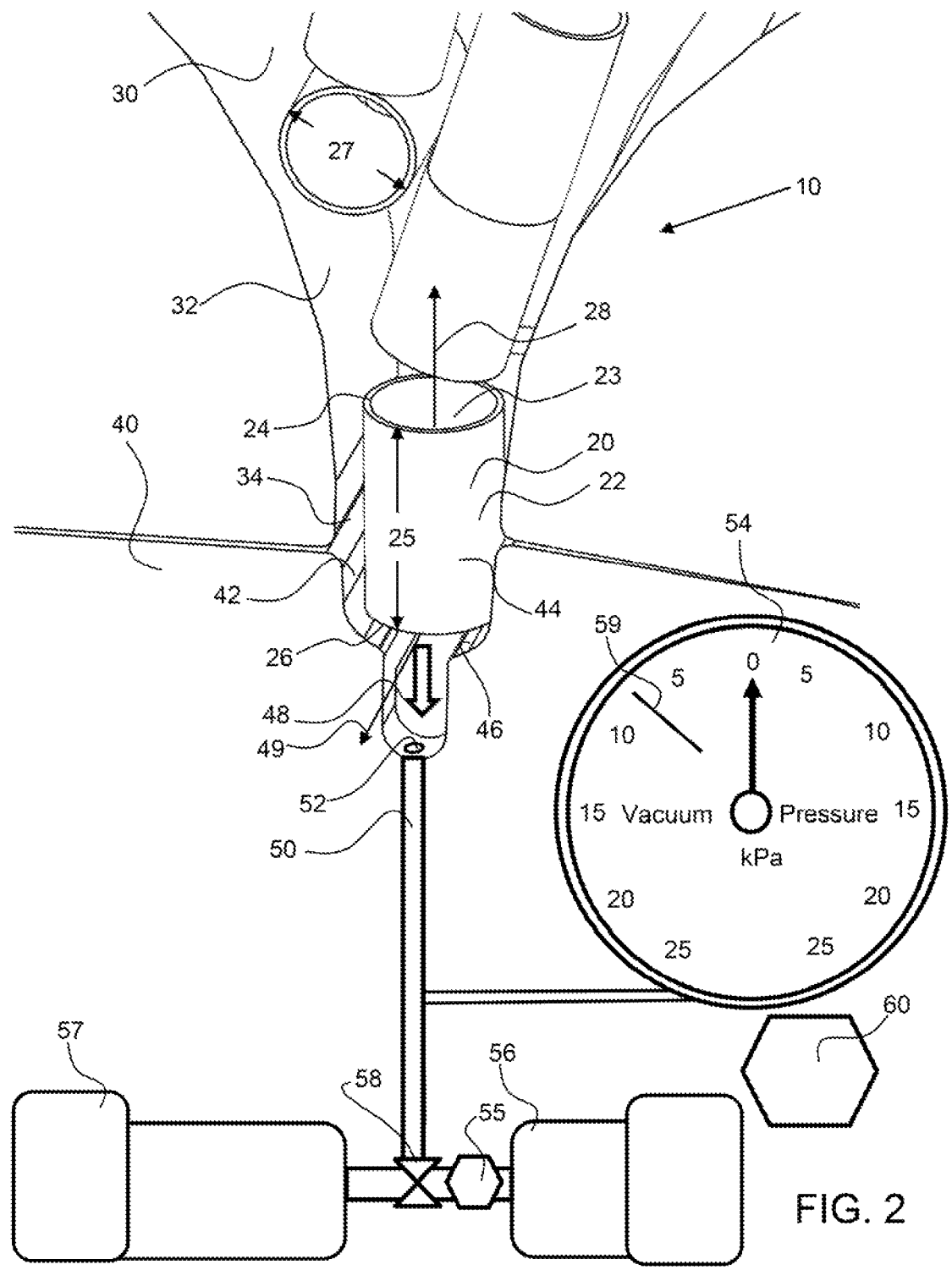
FIG. 2 shows an enlarged perspective view of the hopper aligned with the band receiver and a marker band not properly positioned in the band receiver; a vacuum is being drawn to determine if a marker band is properly located in the band receiver.

Referring now to FIGS. 2 to 6, an exemplary marker band locator system 10 has a hopper 30 for retaining a plurality of marker bands 20 and a band receiver 42 configured in an indexer 40 to retain a properly located marker band 21 for movement to a secondary position for further processing. As shown in FIG. 2, a marker band 20 is cylindrical in shape having a cylindrical wall 22, a conduit 23, a length 25 from a first end 24 to a second end 26, a length axis extending along a center of the conduit and aligned with the length, and an outer diameter 27.

As shown in FIG. 2, a marker band 20 is not properly located in the band receiver 42 as the length 25 and length axis 28 are not aligned with the length axis 49 of the curved seal surface 46 of the band receiver, a recess in the indexer 40. This curved seal surface may have a radius of curvature that corresponds with the outer diameter of the marker band for producing a seal and the length axis extends along the length 94 of the curved seal surface, as best shown in FIG. 4, wherein the length extends tangentially along the curved seal surface from the front to the back of the curved seal surface. A vacuum, as indicated by the bold downward arrow, is being drawn in the band receiver, such as by the vacuum source 57, but since the improperly located marker band does not block the band inlet opening 44, or the pressure well 48, the vacuum pressure value does not exceed a required threshold vacuum pressure level 59 as indicated on the pressure gauge. The length 25 and length axis 28 of the improperly marker band are not aligned with the length and length axis 49 of the curved seal surface 46. The controller 60 may receive input from the pressure gauge and therefore initiate a burst of pressure to jostle the marker bands to re-position them, as shown in FIGS. 3 and 4.

Figure 3:
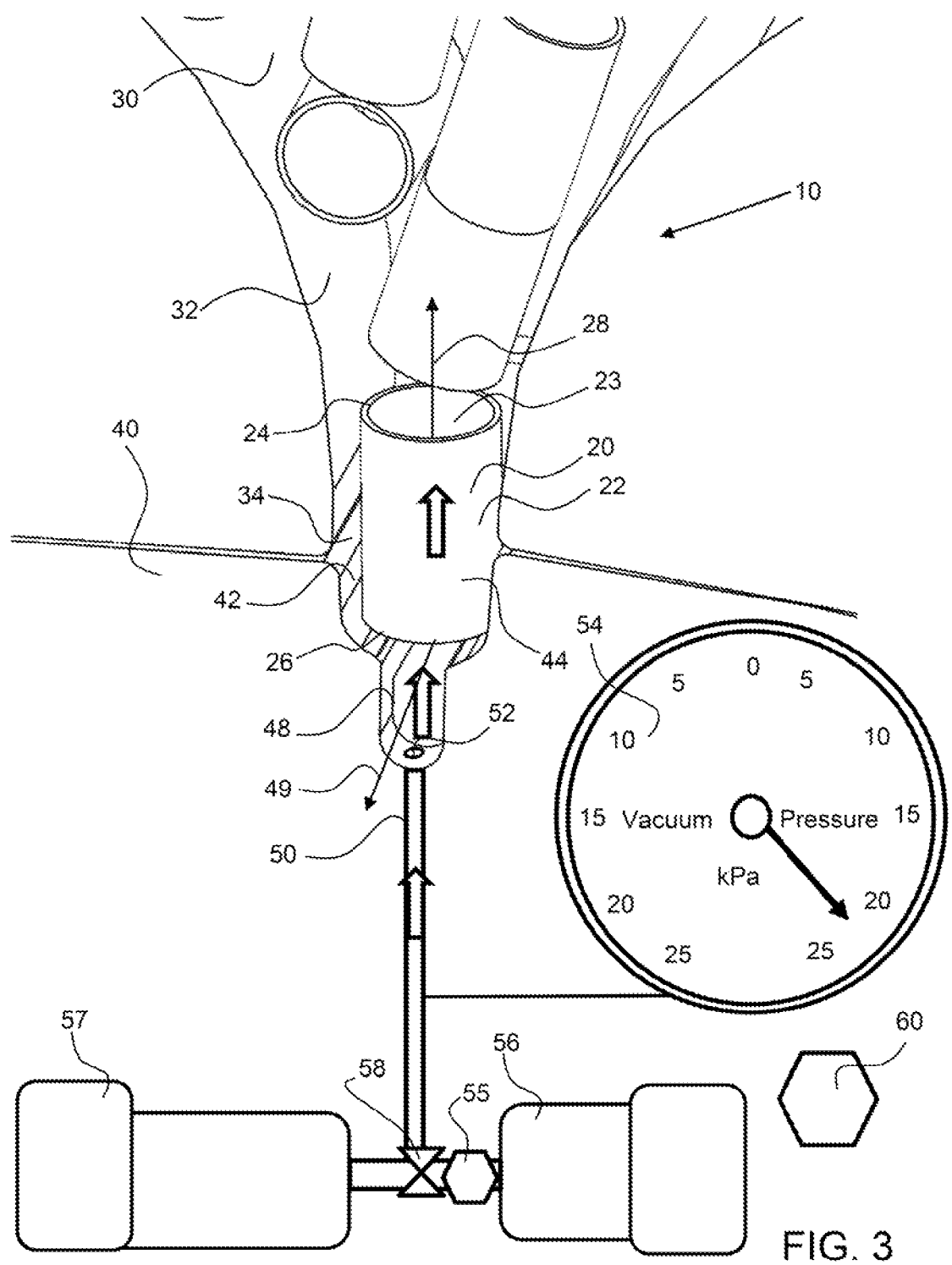
FIG. 3 shows an enlarged perspective view of the hopper aligned with the band receiver and a burst of pressure from the pressure port to jostle and rearrange the marker bands in the hopper.
Figure 4:
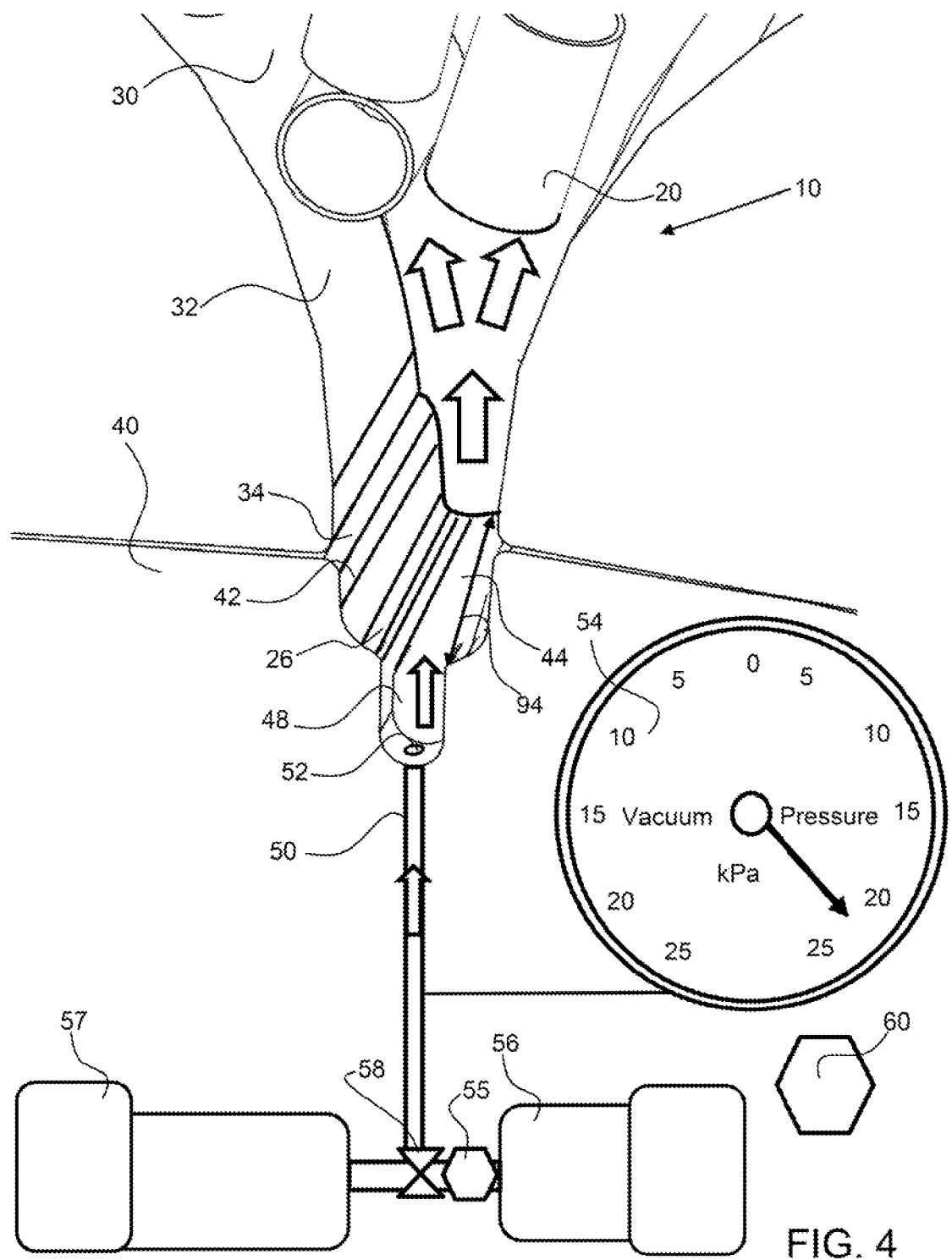
FIG. 4 shows an enlarged perspective view of the hopper aligned with the band receiver and burst of pressure from the pressure port that has lifted the maker bands out of the hopper funnel so that they can resettle through the hopper funnel and into the band receiver for another pressure check.
Figure 5:
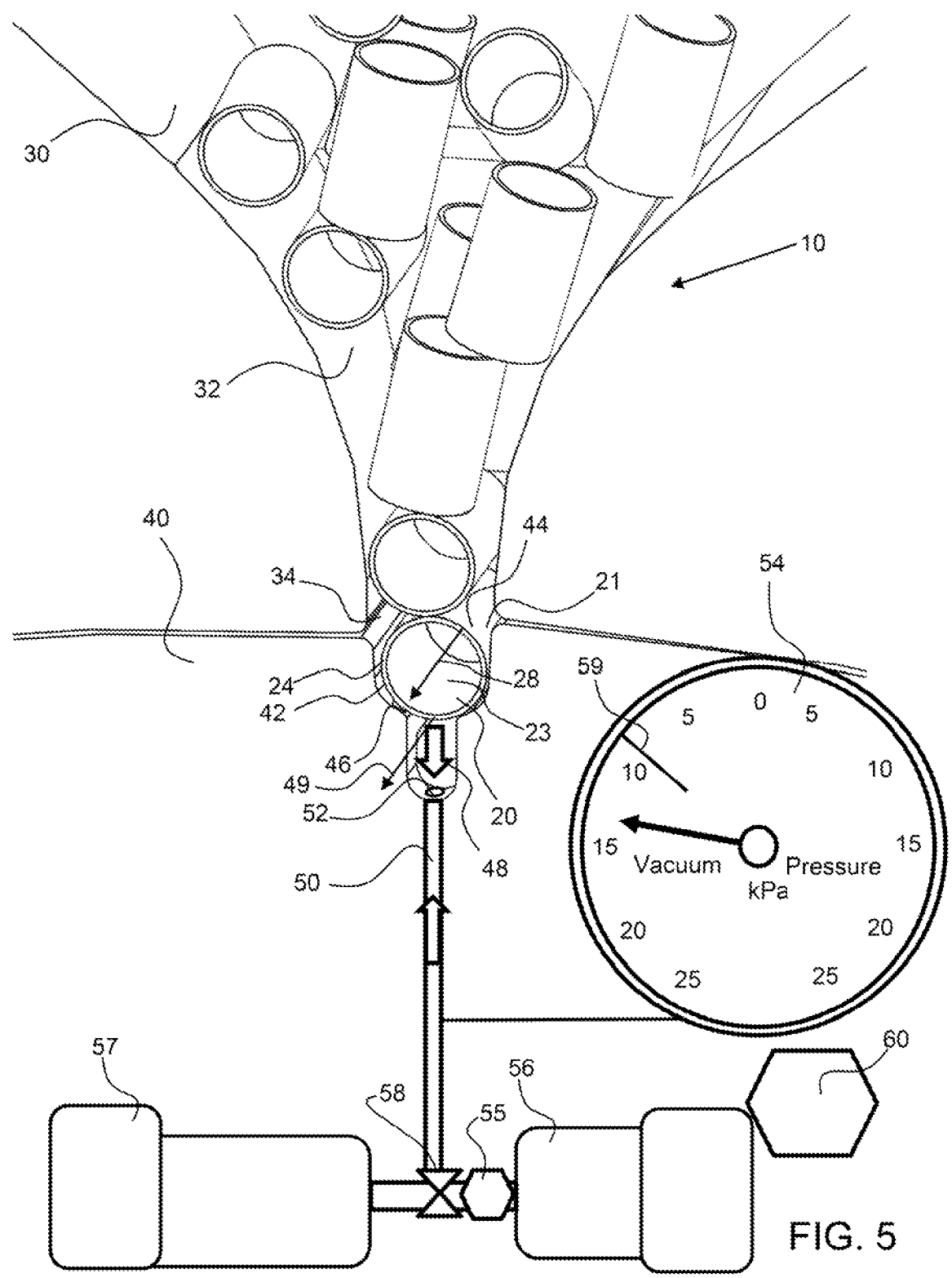
FIG. 5 shows an enlarged perspective view of the hopper aligned with the band receiver and a marker band now properly positioned in the band receiver; a vacuum is being drawn to produce a vacuum pressure in the pressure line that is above a threshold value.

As shown in FIG. 3 and FIG. 4, the improperly located maker band 20 is lifted out of the band receiver 42 and the maker bands are blown out of the hopper funnel 32. Upon resettling when the burst of air ceases, a marker band may settle in the band receiver properly. A gas pressure source 56 provides the pressurized gas, such as air, and a regulator 55 may be used to regulate the burst of pressure required to effectively jostle the marker bands. A valve 58 may switch flow in the pressure line 50 between the pressure source 56 and the vacuum source 57 until a marker band is properly located and the vacuum pressure is above the threshold value 59, as shown in FIG. 5. This cycle of vacuum test and burst of air may be repeated until a marker band is properly located in the band receiver. Each cycle may be very rapid, such as a second or less as described herein.

As shown in FIG. 5, vacuum is being drawn through the pressure line 50 to produce a vacuum in the pressure well 48 created by the seal formed between the marker band 20 and the curved seal surface 46 of the band receiver 42. Note that the length axis 28 and the length axis of the curved seal surface 49 are aligned. The vacuum pressure is above the threshold vacuum pressure level 59, as indicated by the pressure gauge 54. This indicates that there is a properly located marker band 21 in the band receiver. The outer diameter of the marker band rests on the curved seal surface 46 of the band receiver 42. The pressure well 48 extends down from the curved seal surface and the pressure port 52 is coupled with the pressure well. With the marker band properly positioned, a seal is created between the marker band and the band receiver over the pressure well. The controller 60 may receive input from the pressure gauge and then move the band receiver, and a located marker band therein, to a secondary position for further processing or removal.

Figure 6:
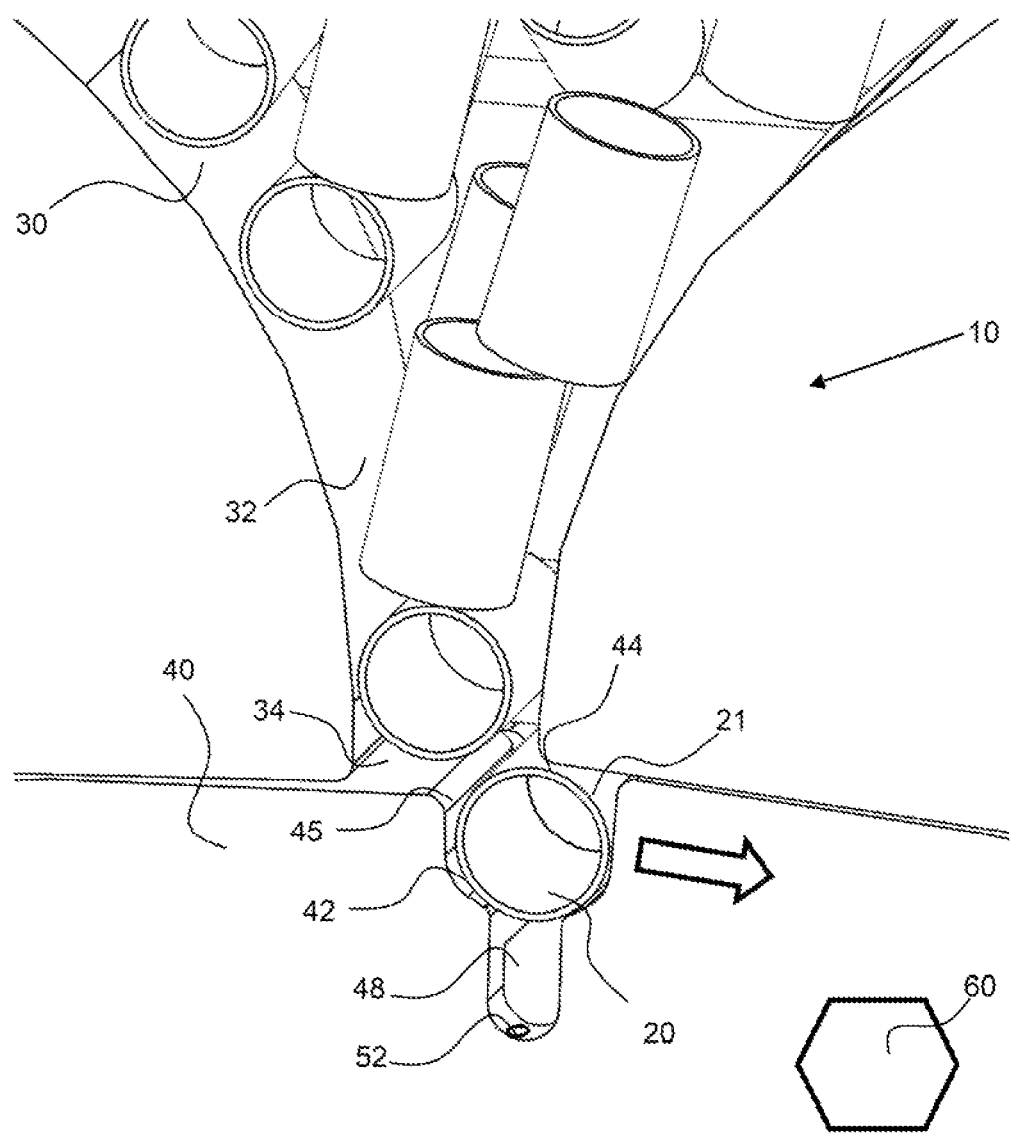
FIG. 6 shows an enlarged perspective view the band receiver being actuated from the locating position to move the band receiver and a located marker band therein to a secondary position for further processing.
Figure 7:
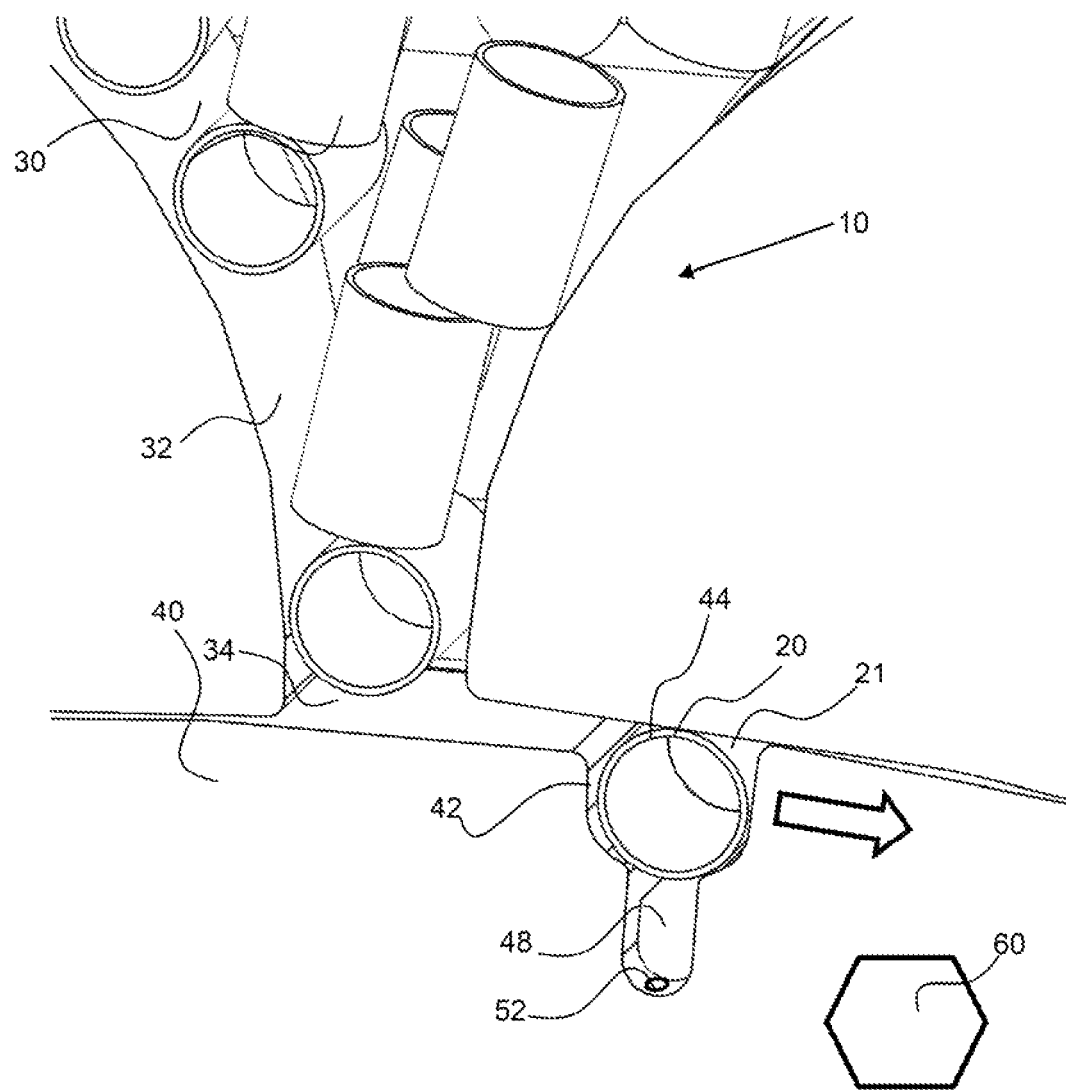
FIG. 7 shows an enlarged perspective view of the band receiver being actuated from the locating position to move the band receiver and a located marker band therein to a secondary position.

As shown in FIGS. 6 and 7, the indexer 40 is being actuated to move the band receiver 42 away from the hopper outlet opening 34.

Figure 8:
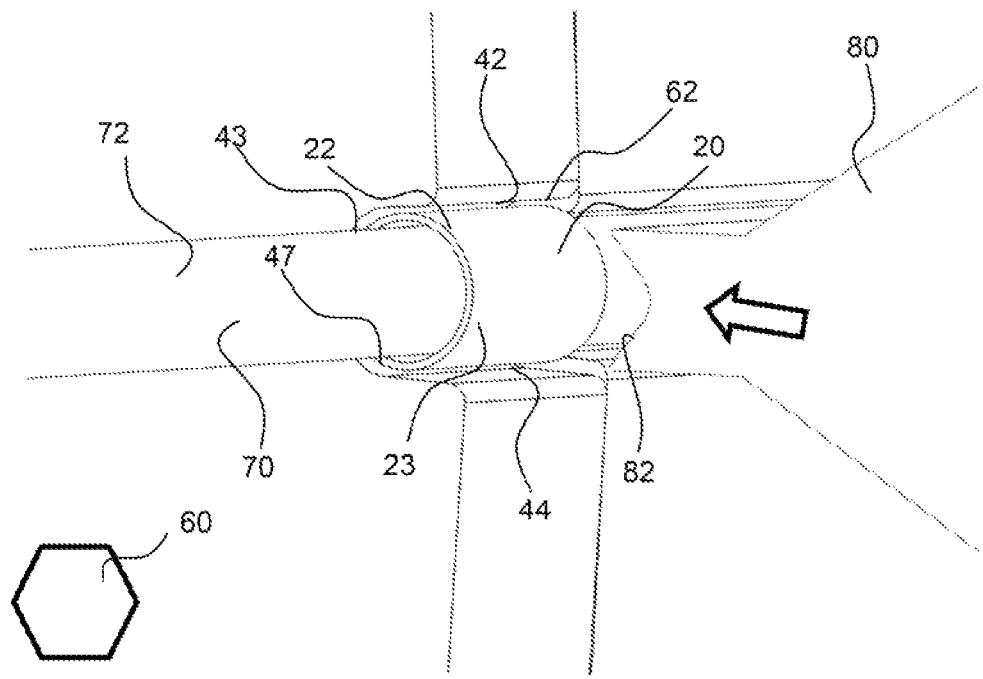
FIG. 8 shows a marker band positioned in a secondary position and a medical device inserted through the marker band.
Figure 9:
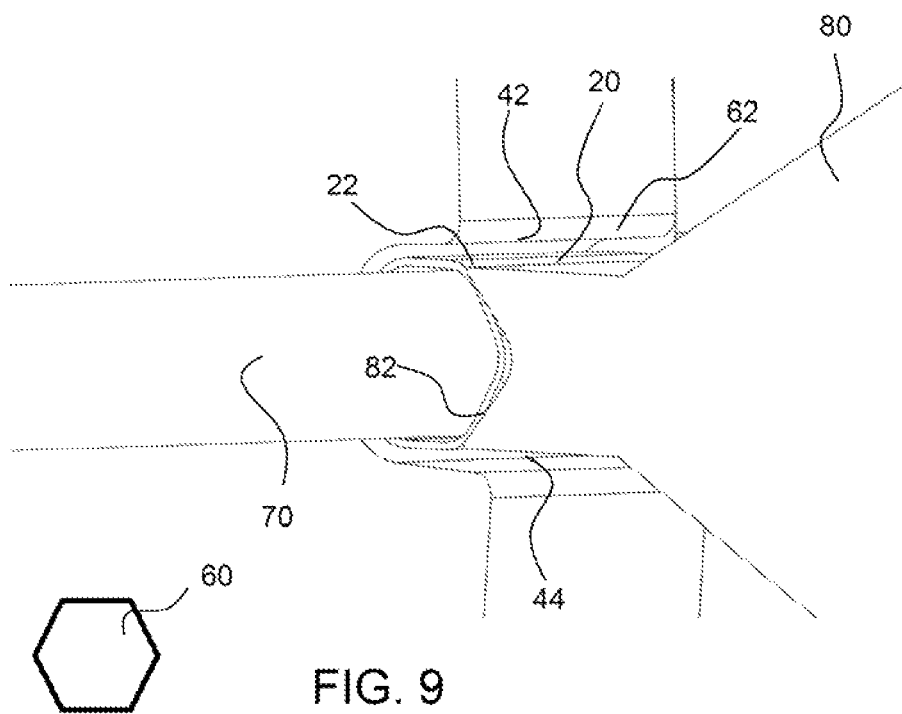
FIG. 9 shows a marker band being crimped onto a medical device by a crimp tool.

As shown in FIGS. 8 and 9, a marker band is now moved to a secondary position 62 where a medical device 70, such as a catheter 72, is inserted through the marker band 20 and a crimp tool 80 is actuated to crimp the marker band onto the medical device. The crimp tool may have two or more flat or planar crimp surfaces 82 to secure the marker band to the medical device. The secondary position may include a receiving funnel 43 and/or alignment bore 47 for positioning and retaining the marker band for further processing, such as inserting a medical device therethrough and crimping the marker band onto the medical device.

Figure 10:
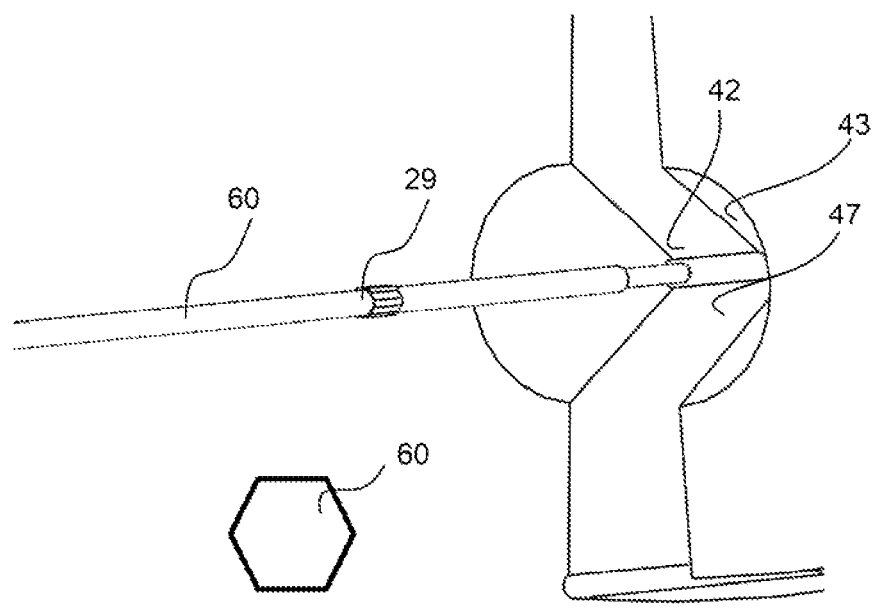
FIG. 10 shows the marker band crimped on the medical device and removed from the band receiver.

As shown in FIG. 10 the medical device 60 and the crimped marker band 29 are moved out of the band receiver 42.

Figure 11:
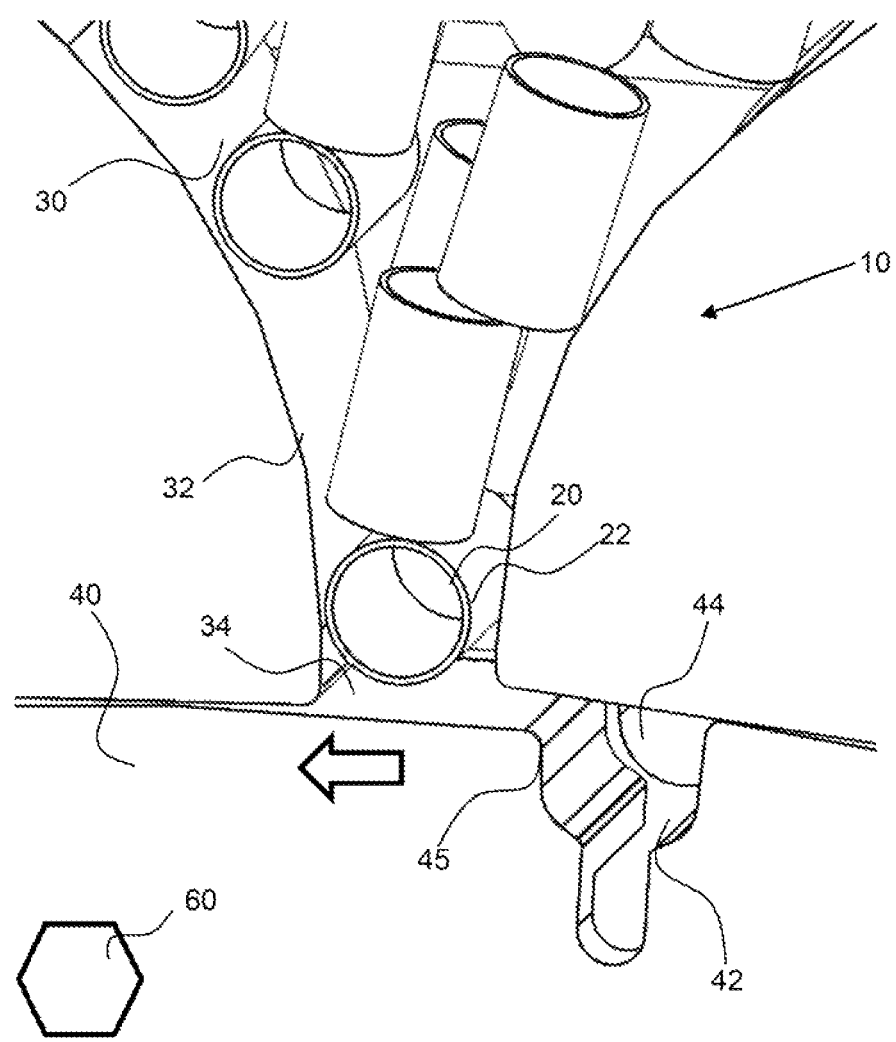
FIG. 11 shows the indexer being moved back to the locating position where the hopper outlet opening is aligned with the band inlet opening of the band receiver.

As shown in FIG. 11, the indexer 40 is being moved back to align the band receiver 42 with the hopper outlet opening 34 to receive another marker band 20. The curved lead surface 45 of the band receiver prevents any marker bands from getting caught and damaged by movement of the band receiver into alignment with the outlet opening of the hopper 30.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A marker band locator system comprising:
  a) a hopper having a hopper outlet opening;
  b) a plurality of marker bands configured in said hopper;
  c) an indexer comprising:
    i) a band receiver having a pressure port;
    ii) an indexer actuator configured to move the band receiver from a locating position to a secondary position;
  wherein in a locating position, the hopper outlet opening is aligned with the band receiver to locate a marker band from said plurality of marker bands in the band receiver;
  d) a pressure source fluidly coupled with the band receiver and configured to produce a flow of gas into the band receiver;
  e) a vacuum source fluidly coupled with the pressure port in the band receiver and configured to produce a flow of gas from a pressure port and a vacuum pressure;
  f) a pressure gauge configured to measure the vacuum pressure;
    wherein when the vacuum pressure is above a threshold vacuum pressure level, the indexer actuator moves the indexer to move a located marker band, located in band receiver, to said secondary position;
    wherein when the vacuum pressure is below a threshold vacuum pressure level said flow of gas into the band receiver is initiated by the pressure source to jostle the plurality of marker bands within the hopper.

2. The marker band locator system of claim 1, further comprising a controller that is coupled with the vacuum source, the pressure source, the pressure gauge and the indexer actuator and configured to receive input from the pressure gauge and control the indexer actuator to move the indexer and control said flow of gas into the band receiver from the pressure source and said flow of gas from the pressure port by the vacuum source;
  wherein when the vacuum pressure is above a threshold vacuum pressure level, indicating that a marker band is property located in the band receiver;
  the controller directs the indexer actuator to move the indexer and said located marker band to said secondary position.

3. The marker band locator system of claim 2, further comprising a valve configured to switch from said flow of gas into the band receiver from the pressure source to said flow of gas from the pressure port to the vacuum source; and
wherein the controller is coupled with the valve to control said valve.

4. The marker band locator system of claim 2, wherein after the plurality of marker bands are jostled by the flow of gas into the band receiver, the controller initiates a flow of gas from the vacuum port by the vacuum source and wherein when the pressure gauge measures a vacuum pressure above said threshold vacuum pressure level the controller initiates the indexer actuator to move the indexer and the located marker band therein to said secondary position.

5. The marker band locator system of claim 1, wherein the marker band in cylindrical in shape having a cylindrical wall and a conduit from a first end to a second end.

6. The marker band locator system of claim 5, wherein the marker band has an outer diameter.

7. The marker band locator system of claim 6, wherein the band receiver has a curved seal surface that is effectively the same as the outer diameter of the marker band to enable the pressure source to produce said vacuum pressure.

8. The marker band locator system of claim 7, wherein the pressure port is configured at the bottom of the band receiver.

9. The marker band locator system of claim 8, wherein the pressure port is configured in a pressure well of the band receiver.

10. The marker band locator system of claim 1, wherein the secondary position is a crimping station and wherein the located marker band is crimped onto a medical device inserted therethrough at the secondary position.

11. The marker band locator system of claim 10, wherein the medical device is inserted a controlled depth through the marker band, thereby locating the crimped marker band at a controlled position on the medical device.

12. The marker band locator system of claim 1, wherein the secondary position has a receiving funnel and alignment bore that locates the medical device to be inserted into the marker band.

13. The marker band locator system of claim 1, wherein the hopper has a hopper funnel that tapers from the hopper to the hopper outlet opening.

14. A method of locating a marker band comprising:
a) providing a marker band locator system comprising:
 i) a hopper having a hopper outlet opening;
 ii) a plurality of marker bands configured in said hopper;
 iii) an indexer comprising:
  a band receiver having a pressure port;
  an indexer actuator configured to move the band receiver from a locating position to a secondary position;
 wherein in a locating position, the hopper outlet opening is aligned with the band receiver to locate a marker band from said plurality of marker bands in the band receiver;
 iv) a pressure source fluidly coupled with the band receiver and configured to produce a flow of gas into the band receiver;
 v) a vacuum source fluidly coupled with the pressure port in the band receiver and configured to produce a flow of gas from pressure port and a vacuum pressure;
 vi) a pressure gauge configured to measure the vacuum pressure;

b) measuring the vacuum pressure;
c) wherein when the vacuum pressure is above a threshold vacuum pressure level, moving the indexer by the indexer actuator to move the indexer and a located marker band, located in band receiver, to a secondary position;
d) wherein when the vacuum pressure is below a threshold vacuum pressure level, initiating said flow of gas into the pressure port by the pressure source to jostle the plurality of marker bands within the hopper and subsequently producing said flow of gas from the pressure port by said vacuum source and measuring the vacuum pressure.

15. The method of claim 12, further comprising providing a controller that is coupled with the vacuum source, the pressure source, the pressure gauge and the indexer actuator and configured to receive input from the pressure gauge and control the indexer actuator to move the indexer and control said flow of gas into the band receiver from the pressure source and said flow of gas from the pressure port by the vacuum source;
wherein when the vacuum pressure is above a threshold vacuum pressure level, indicating that a marker band is properly located in the band receiver;
the controller directs the indexer actuator to move the indexer and said located marker band to said secondary position.

16. The method of claim 13, further comprising providing a valve configured to switch from said flow of gas into the band receiver from the pressure source to said flow of gas from the pressure port to the vacuum source; and
wherein the controller is coupled with the valve to control said valve.

17. The method of claim 13, wherein after the plurality of marker bands are jostled by the flow of gas into the band receiver, the controller initiates a flow of gas from the vacuum port by the vacuum source and wherein when the pressure gauge measures a vacuum pressure above said threshold vacuum pressure level the controller initiates the indexer actuator to move the indexer and the located marker band therein to said secondary position.

18. The method of claim 12, wherein the marker band in cylindrical in shape having a cylindrical wall and a conduit from a first end to a second end.

19. The method of claim 16, wherein the marker band has an outer diameter.

20. The method of claim 17, wherein the band receiver has a curved seal surface that is effectively the same as the outer diameter of the marker band to enable the pressure source to produce said vacuum pressure.

21. The method of claim 18, wherein the pressure port is configured at the bottom of the band receiver.

22. The method of claim 19, wherein the pressure port is configured in a pressure well of the band receiver.

23. The method of claim 12, wherein the hopper has a hopper funnel that tappers from the hopper to the hopper outlet opening.

24. The method of claim 12, wherein the secondary position is a crimping station and wherein the located marker band is crimped onto a medical device inserted therethrough at the secondary position.

25. The method of claim 24, wherein the medical device is inserted a controlled depth through the marker band, thereby locating the crimped marker band at a controlled position on the medical device.

26. The method of claim 12, wherein the secondary position has a receiving funnel and alignment bore that locates the medical device to be inserted into the marker band.

\* \* \* \* \*